US012653584B2

(12) United States Patent
Baccelli et al.

(10) Patent No.: US 12,653,584 B2
(45) Date of Patent: Jun. 16, 2026

(54) VERTEBRAL IMPLANT FOR DYNAMIC STABILIZATION

(71) Applicant: COMPANION SPINE, Mérignac (FR)

(72) Inventors: Christian Baccelli, Saucats (FR); Jacques Senegas, Mérignac (FR)

(73) Assignee: Companion Spine France, Mérignac (FR)

( * ) Notice: Subject to any disclaimer, the term of this patent is extended or adjusted under 35 U.S.C. 154(b) by 114 days.

(21) Appl. No.: 18/597,447

(22) Filed: Mar. 6, 2024

(65) Prior Publication Data

US 2024/0315738 A1 Sep. 26, 2024

(30) Foreign Application Priority Data

Mar. 7, 2023 (FR) ........................................ 2302100

(51) Int. Cl.
*A61B 17/70* (2006.01)
*A61B 17/00* (2006.01)

(52) U.S. Cl.
CPC ...... *A61B 17/7062* (2013.01); *A61B 17/7053* (2013.01); *A61B 2017/00955* (2013.01)

(58) Field of Classification Search
CPC . A61B 17/70; A61B 17/7062; A61B 17/7064; A61B 17/7065; A61B 17/7067; A61B 17/7068; A61B 17/707; A61B 17/7053; F16G 11/048; B63B 21/08; F16B 21/165; F16B 21/16
See application file for complete search history.

(56) References Cited

U.S. PATENT DOCUMENTS

| | | | | | |
|---|---|---|---|---|---|
| 626,230 | A | * | 6/1899 | Hawes | F16G 11/10 |
| | | | | | 24/134 P |
| 1,066,751 | A | * | 7/1913 | Park | F16G 11/10 |
| | | | | | 403/390 |
| 1,857,437 | A | * | 5/1932 | Cole | F16G 11/06 |
| | | | | | 24/134 P |
| 1,962,964 | A | * | 6/1934 | Morrison | F16G 11/101 |
| | | | | | 24/134 P |

(Continued)

FOREIGN PATENT DOCUMENTS

| | | | | |
|---|---|---|---|---|
| EP | 1009311 | B1 | 9/2003 | |
| FR | 3047657 | A1 | 8/2017 | |
| WO | WO-2024184480 | A1 * | 9/2024 | ......... A61B 17/7062 |

OTHER PUBLICATIONS

International Search Report and Written Opinion for corresponding International Appl. No. PCT/EP2024/056069 mailed Jun. 6, 2024 (14 pages).

*Primary Examiner* — Jacqueline T Johanas
(74) *Attorney, Agent, or Firm* — Farber LLC

(57) ABSTRACT

An intervertebral implant for stabilizing adjacent first and second interspinous processes. The implant includes a spacer having a latch housing wall that extends from a first surface towards a second surface so as to define a latch housing within the spacer. The spacer also has first and second sides each configured to engage a respective one of the first and second adjacent interspinous processes. The spacer may define multiple slots configured to receive portions of a flexible strap for wrapping around the first and second adjacent interspinous processes. A latch may be configured to rotate within the latch housing about a latch axis between first and second rotated positions.

20 Claims, 4 Drawing Sheets

(56) References Cited

U.S. PATENT DOCUMENTS

| | | | | |
|---|---|---|---|---|
| 3,644,966 | A * | 2/1972 | Higgins | F16G 11/14 |
| | | | | 24/134 P |
| 5,070,805 | A * | 12/1991 | Plante | F16G 11/101 |
| | | | | 24/134 P |
| 5,408,729 | A * | 4/1995 | Schwartz | F16G 11/14 |
| | | | | 24/132 WL |
| 6,053,921 | A * | 4/2000 | Wagner | A61B 17/8869 |
| | | | | 606/103 |
| 6,099,527 | A | 8/2000 | Hochschuler | |
| 8,012,209 | B2 | 9/2011 | Kyphon | |
| 8,221,464 | B2 * | 7/2012 | Belliard | A61B 17/7062 |
| | | | | 606/248 |
| 9,924,984 | B2 * | 3/2018 | Hartdegen | A61B 17/8863 |
| 10,595,910 | B2 * | 3/2020 | Senegas | A61B 17/7064 |
| 11,166,755 | B2 * | 11/2021 | Cianfrani | A61B 17/8042 |
| 11,413,074 | B2 * | 8/2022 | Lutz | A61B 17/7062 |
| 2005/0122419 | A1 * | 6/2005 | Yoon | H04N 23/55 |
| | | | | 348/E5.025 |
| 2005/0252269 | A1 * | 11/2005 | Sawdon | B21D 39/031 |
| | | | | 72/451 |
| 2009/0292317 | A1 * | 11/2009 | Belliard | A61B 17/7062 |
| | | | | 606/279 |
| 2010/0121387 | A1 * | 5/2010 | Belliard | A61B 17/8861 |
| | | | | 606/86 A |
| 2011/0254450 | A1 * | 10/2011 | Bergholz | H05B 45/58 |
| | | | | 315/121 |
| 2013/0030465 | A1 * | 1/2013 | Hess | A61B 17/8004 |
| | | | | 606/246 |
| 2019/0099206 | A1 * | 4/2019 | Senegas | A61F 2/44 |
| 2020/0080620 | A1 * | 3/2020 | Graber | E04F 11/1842 |
| 2020/0107864 | A1 * | 4/2020 | Senegas | A61B 17/7083 |
| 2020/0170685 | A1 * | 6/2020 | Lutz | A61B 17/8869 |
| 2022/0151662 | A1 | 5/2022 | Murray | |

* cited by examiner

VERTEBRAL IMPLANT FOR DYNAMIC STABILIZATION

CROSS-REFERENCE TO RELATED APPLICATIONS

This application claims the benefit of priority under 35 U.S.C. 119(a) to French patent application no. FR 2302100, filed Mar. 7, 2023, the entire disclosure of which is incorporated herein by reference for all purposes.

TECHNICAL FIELD

The present disclosure relates to the field of implants used in spinal surgery, and more particularly, to vertebral implants for stabilizing adjacent first and second interspinous processes.

BACKGROUND

Operations in the field of spinal surgery may involve the cervical (neck), dorsal or, more frequently, lumbar region.

Where there is instability, such as slippage of a vertebra in relation to adjacent vertebrae, spinal stabilization devices may be employed. Such spinal stabilization devices may include intervertebral implants consisting of a stabilizing spacer, a flexible textile braid-type strap, a mobile assembly and a locking member. The stabilizing spacer is intended to be placed between the spinous processes of two consecutive, i.e. adjacent, vertebrae to be stabilized. The flexible strap (e.g. a textile braid) encloses the spinal processes. The movable assembly is adapted to engage with the stabilizing spacer so as to lock the flexible strap in place relative to the stabilizing spacer. This is achieved by pinching the flexible strap between the movable assembly and the stabilizing spacer. The locking member (e.g. a screw) is adapted to lock the engagement of the moving assembly with the stabilizing spacer, thereby resulting in the the final locking of the flexible strap.

Examples of such implants can be found in, e.g., EP 1009311 B1. In the devices of EP 1009311, a spacer is fitted with a flexible strap that forms a loop. The flexible strap is locked by a quarter-turn rotary latch that may be maneuvered inside the spacer. This device, however, does not ensure a correct locking of the flexible strap, as the positioning of the rotary latch in its locked position is not ensured, particularly in the case where the flexible link is a flat strap over which the rotary latch may slide and turn.

Another example of an intervertebral implant is described in FR 3047657 A1, in the name of the present applicant. In this device, an implant is described comprising a stabilizing spacer, adapted to stabilize at least two adjacent vertebrae together by being secured between the spinous processes of the vertebrae. The spacer includes a recess provided with a longitudinal axis and receiving radially on at least one side of the recess at least one portion of a flexible strap. The flexible strap fixes the stabilizing spacer to the spinous processes of the vertebrae to be stabilized. The implant includes a blocking pin having a longitudinal axis and a profile substantially complementary to the shape of the recess. The blocking pin is configured to be displaced in the direction of the longitudinal axis inside the recess, and to lock the strap by pinching the latter between the blocking pin and the inner wall of the recess. This device also includes a locking screw that is coaxial with the blocking pin. The locking screw must be inserted into the recess after the flexible strap has already been positioned.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

In accordance with an exemplary aspect of the disclosure, there is provided an intervertebral implant for stabilizing adjacent first and second interspinous processes. The implant may include a spacer having a first surface opposite a second surface, the spacer having a latch housing wall that extends from the first surface towards the second surface so as to define a latch housing within the spacer. The spacer may have a first side opposite a second side, the first and second sides each configured to engage a respective one of the first and second adjacent interspinous processes. The spacer may also define first, second and third slots each extending through the spacer from the first side to the second side. Each of the first, second and third slots may be configured to receive portions of a flexible strap for wrapping around the first and second adjacent interspinous processes. The implant may also include a latch secured within the latch housing and configured to rotate about a latch axis between first and second rotated positions within the latch housing, the latch having first and second faces each positioned at different distances from the axis. When the latch is in the first rotated position, the first face of the latch may face the latch housing wall at a distance from the latch housing wall that is greater than the thickness of the flexible strap such that the strap is free to move between the first face of the latch and the latch housing wall. When the latch is in the second rotated position, the second face of the latch may face the latch housing wall at a distance from the latch housing wall that is less than the thickness of the flexible strap such that the strap is restricted from moving by and between the second face of the latch and the latch housing wall.

According to some embodiments, the latch may include, at a first end, a head defining a tool-receiving opening, the tool-receiving opening configured to be engaged by a tool so as to rotate the latch between its first and second rotated positions. The head of the latch may include a head surface having at least one notch defined therein. The implant may also include a locking mechanism maintained within the spacer. The locking mechanism may be movable within the spacer such that, when the latch is in the first rotated position the locking mechanism engages the head surface without entering the notch, and when the latch is in the second rotated position the locking mechanism enters the notch so as to prevent the latch from further rotation.

According to some embodiments, the locking mechanism may be a spring rod fixed at one end within the spacer, the other end of the spring rod being movable into the notch. Advantageously, the locking mechanism may include two spring rods disposed on opposite sides of the latch housing. The latch head may include a plurality of notches defined around its circumference, such that the spring rods can move into any one of the plurality of notches so as to lock the latch relative to the latch housing in a plurality of different rotational positions. The latch may include, at an end opposite from the head, a ferrule that maintains the latch within the latch housing.

According to some embodiments, the first face of the latch may be flat. The latch may include two such flat first latch faces that are disposed on opposite sides of the latch relative to each other, the two flat latch faces being at a first latch face distance from each other. In addition, the first and second slots may be spaced at a slot distance from each other, the first and second slots may intersect with the latch housing, and the first latch face distance may be less than or equal to the first slot distance, such that the flexible strap is free to move across both of the flat first latch surfaces. In embodiments, the second face of the latch and the latch wall may both be curved so as to be complementary relative to each other.

In accordance with another exemplary aspect of the disclosure, there is provided an intervertebral implant for stabilizing adjacent first and second interspinous processes. The implant may include a spacer having a first side opposite a second side, the first and second sides each configured to engage a respective one of the first and second adjacent interspinous processes. The spacer may have first and second surfaces opposite to each other and perpendicular relative to the first and second sides, and the spacer may have a latch housing wall that extends from the first surface towards the second surface so as to define a latch housing within the spacer. The spacer may also define at least one slot extending through the spacer from the first side to the second side. The at least one slot may intersect with the latch housing, and the at least one slot may be configured to receive a portion of a flexible strap for wrapping around one or both of the first and second adjacent interspinous processes. The implant may also include a latch positioned within the latch housing and configured to rotate about a latch axis between a first rotated position at which the strap is free to move between the latch and the latch housing wall, and a second rotated position at which the strap is restricted from moving between the latch and the latch housing wall. The latch may also include a locking mechanism maintained within the spacer and configured to selectively engage the latch so as to prevent the latch from rotating within the latch housing when the latch is in the second rotated position.

According to some embodiments, the latch may have a head adjacent to the first surface of the spacer, the head defining a notch. The locking mechanism may be a spring rod that is fixed at one end within the spacer, the other end of the spring rod being movable into the notch. The spacer may define a channel in which the spring rod resides. When the latch is rotated to a position at which the notch is aligned with the channel, at least a portion of the spring rod may move from the channel into the notch to prevent the latch from further rotating within the latch housing.

According to some embodiments, the locking mechanism may include two such spring rods, disposed on opposite sides of the latch housing. The latch head may include a plurality of notches defined around its circumference, such that the spring rods can move into any one of the plurality of notches so as to lock the latch relative to the latch housing in a plurality of different rotational positions.

According to some embodiments, the latch may have first and second faces each positioned at different distances from the axis. Thus, when the latch is in the first rotated position, the strap may be free to move between the first face of the latch and the latch housing wall because the first face of the latch faces the latch housing wall at a distance from the latch housing wall that is greater than the thickness of the flexible strap. In addition, when the latch is in the second rotated position, the strap may be restricted from moving between the second face of the latch and the latch housing wall because the second face of the latch faces the latch housing wall at a distance from the latch housing wall that is less than the thickness of the flexible strap.

According to some embodiments, the at least one slot may include two such slots, the flexible strap having a first portion extending through one slot and having a second portion extending through the other slot. Both portions of the flexible strap that extend through the two slots may be configured to be restricted from moving between second faces of the latch and the latch housing wall. In addition, the spacer may also define a third slot, a third portion of the flexible strap extending through the third slot. The flexible strap may form between the second and third slots a first loop around a first one of the adjacent interspinous processes, and the flexible strap may also form between the third and first slots a second loop around a second one of the adjacent interspinous processes.

According to some embodiments, the latch may include a tool-receiving opening, the tool-receiving opening configured to be engaged by a tool so as to rotate the latch between its first and second rotated positions. The latch may also include, at an end opposite from the head, a ferrule that maintains the latch within the latch housing. In embodiments, the first face of the latch may be flat. Additionally or alternatively, the second face of the latch and the latch wall may both be curved.

BRIEF DESCRIPTION OF THE DRAWINGS

Further features, details and advantages will become apparent from the detailed description below, and from an analysis of the appended drawings, wherein.

DETAILED DESCRIPTION

Reference will now be made in detail to specific embodiments illustrated in the accompanying drawings. In the following detailed description, numerous specific details are set forth to provide a thorough understanding. However, it will be apparent to one of ordinary skill in the art that embodiments may be practiced without these specific details. In other instances, known methods, procedures and/or components have not been described in detail so as not to unnecessarily obscure aspects of the embodiments.

Figure 1A:
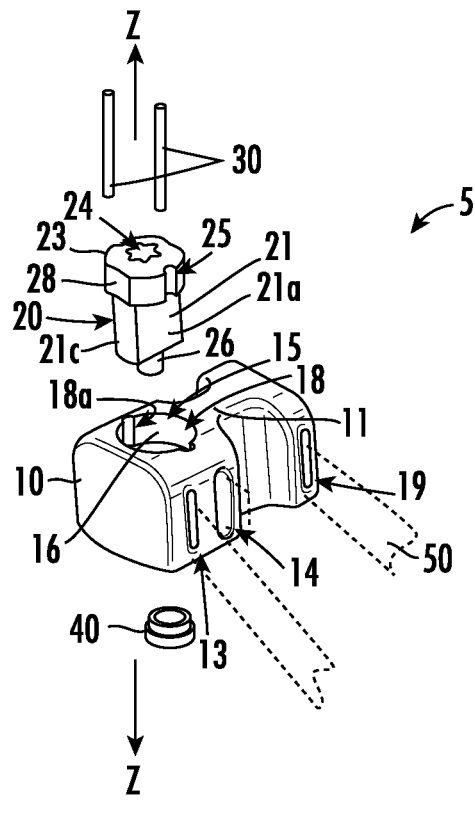
FIG. 1A shows an exploded perspective view of an implant, according to various embodiments of the disclosure.
Figure 1B:
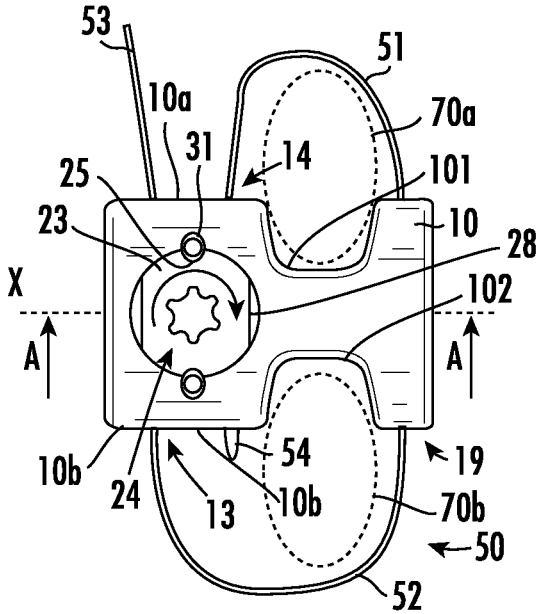
FIG. 1B shows a front view of the implant of FIG. 1A in the locked position.

Reference is now made to FIG. 1A, which shows a vertebral implant 5 for dynamic vertebral stabilization, and more specifically for stabilizing adjacent first and second interspinous processes (not shown in FIG. 1A, but shown in FIG. 1B). According to this embodiment, the implant 5 includes a spacer 10, a rotating latch 20 and a strap 50 (shown in dotted line). In accordance with some embodiments, the spacer 10 may be made formed from a biocompatible polymer such as PEEK, and the latch 20 may be formed from stainless steel or titanium.

Figure 2:
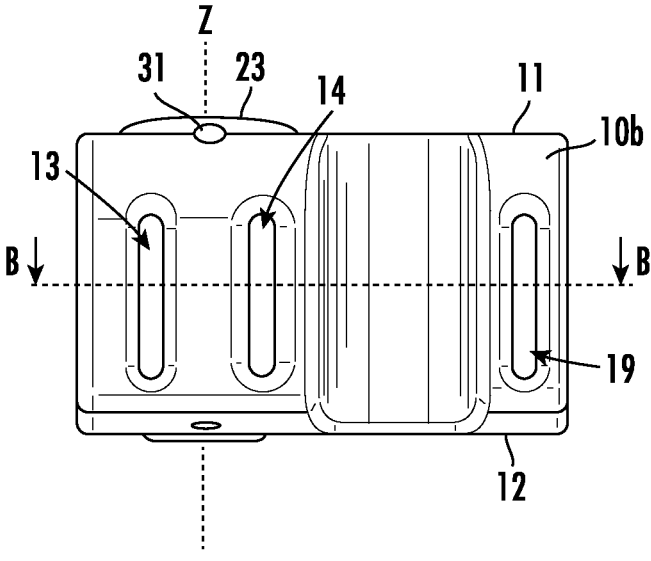
FIG. 2 shows a side view of the implant of FIG. 1A.

The spacer 10 includes a first surface 11 opposite a second surface 12 (best shown in, e.g., FIG. 2). In addition, the spacer 10 has a latch housing wall 16 (also shown in, e.g., FIG. 5) that extends from the first surface 11 towards the second surface 12 so as to define a latch housing 15 within the spacer 10. The latch housing 15 may have a variety of shapes, but is shown in the accompanying figures as having a generally cylindrical bore shape.

The spacer 10 also has a first side 10a opposite a second side 10b (best shown in, e.g., FIG. 1B). Referring to FIG. 1B, the first and second sides 10a, 10b are each configured to engage a respective one of the first and second adjacent interspinous processes (shown schematically as 70a, 70b in dotted line, respectively). More specifically, in the orientation shown in FIG. 1B (which illustrates the spacer 10 oriented as it would be if implanted in a patient's body in the standing position), the first side 10a has a recess 101 that is configured to receive therein a lower edge of an upper one of the adjacent interspinous processes 70a, while the second side 10b has a recess 102 that is configured to receive therein an upper edge of a lower one of the adjacent interspinous processes 70b.

The spacer 10 also defines one or more slots therein. For example, in the embodiments shown in all figures, the spacer 10 defines a first slot 13, a second slot 14 and a third slot 19. Each of the three slots 13, 14, 19 extend through the spacer 10 from the first side 10a to the second side 10b. In addition, in the embodiment shown, each of the first, second and third slots 13, 14, 19 are configured to receive portions of a flexible strap 50 for engaging, e.g., wrapping around, the first and second adjacent interspinous processes, as will be described further below.

Still further, referring to FIG. 1A, the implant 5 includes a latch 20. The latch 20 is secured (as will be described in additional detail below) within the latch housing 15 and is configured to rotate about a latch axis Z. The latch 15 is rotatable between a first rotated position (shown and described in more detail in connection with FIGS. 3 and 5) and a second rotated position (shown and described in more detail in connection with FIGS. 4 and 6) within the latch housing 20.

The latch 20 may have various different shapes, but in the embodiment shown, has a generally blade-shaped configuration that has multiple faces. For example, the latch may have four faces including two opposite-disposed faces 21a, 21b having a first shape and two oppositely-disposed faces 21c, 21d having a second shape. Advantageously, as will be shown and described in further detail below, the first and second-shaped faces may be positioned at different distances from the longitudinal axis Z.

Figure 5:
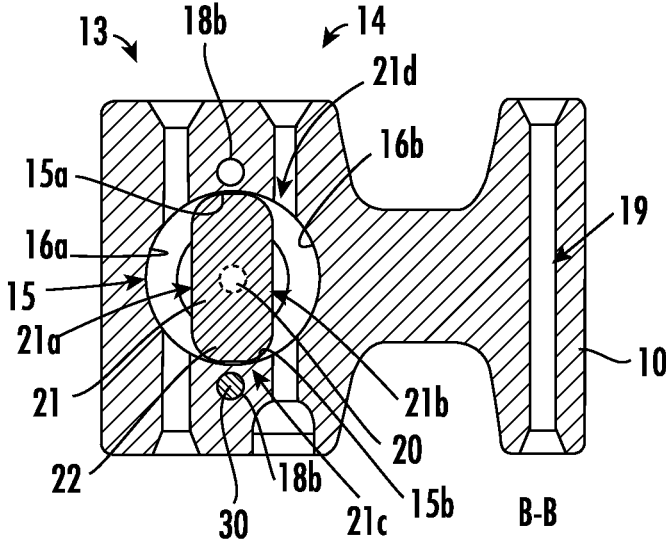
FIG. 5 shows a cross-sectional front view of the implant of FIG. 1A in the release position.

Referring briefly to FIG. 5, there is shown the latch 20 in the first above-described rotated position. As shown in FIG. 5, in this first rotated position, the latch 20 is positioned such that the first faces 21a, 21b of the latch 20 each face respective curved regions 16a, 16b of the latch housing wall 16. The first faces 21a, 21b of the latch 20 are shown as being flat. In addition, in this first rotated position, each of the first faces 21a, 21b of the latch 20 are at a distance (from the respective curved regions 16a, 16b of the latch housing wall 16) that is greater than the thickness of the flexible strap

Figure 1C:
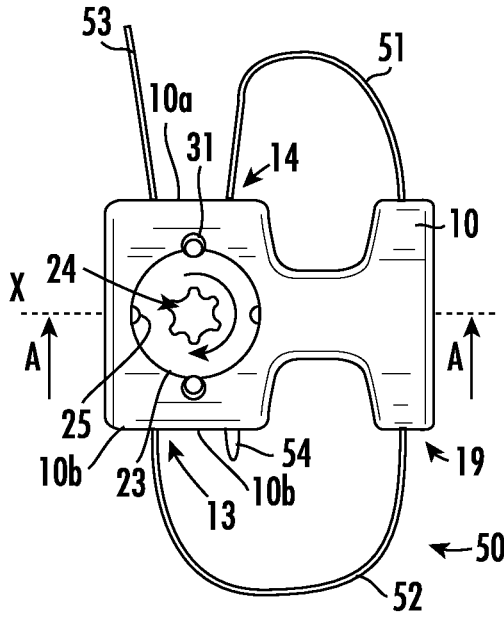
FIG. 1C shows a front view of the implant of FIG. 1A in the unlocked position.

50 (the strap 50 not being shown in FIG. 5, but shown, e.g., in FIGS. 1A through 1C). In this way, in this first rotated position of the latch 20, the strap 50 has sufficient clearance between the first faces 21a, 21b of the latch 20 and the respective curved regions 16a, 16b of the latch housing wall 16 so as to be able to move between the first faces 21a, 21b of the latch 20 and the respective curved regions 16a, 16b of the latch housing wall 16.

Figure 6:
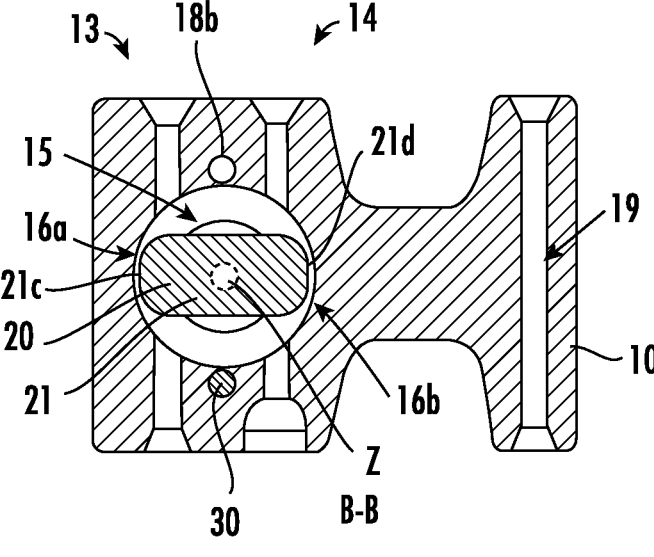
FIG. 6 shows a cross-sectional front view of the implant of FIG. 1A in a locked position.

Referring briefly to FIG. 6, there is shown the latch 20 in the second above-described rotated position. As shown in FIG. 6, in this second rotated position, the latch 20 is positioned such that the second faces 21c, 21d of the latch 20 each face respective curved regions 16a, 16b of the latch housing wall 16. The second faces 21c, 21d of the latch may be curved (e.g., complementary to the curved regions 16a, 16b of the latch housing 16) or may be triangular or corrugated depending on, e.g., the retention strength required. In addition, in this second rotated position, each of the second faces 21a, 21b of the latch 20 are at a distance (from the respective curved regions 16a, 16b of the latch housing wall 16) that is less than the thickness of the flexible strap 50 (again, the strap 50 is not shown in FIG. 5, but is shown, e.g., in FIGS. 1A through 1C). In this way, in this second rotated position of the latch 20, the strap 50 does not have sufficient clearance between the second faces 21a, 21b of the latch 20 and the respective curved regions 16a, 16b of the latch housing wall 16, such that the strap 50 is restricted from moving by and between the second faces 21c, 21d of the latch 20 and the respective curved regions 16a, 16b of the latch housing wall 16.

Referring back to FIG. 1A, the latch 20 may include, at its first end, a head 23 defining in a face thereof, a tool-receiving opening 24. The tool-receiving opening 24 is configured to be engaged by a tool (not shown, but which may be a rotating maneuvering tool, such as a hexalobular, hexagonal, or other screwdriver) so as to rotate the latch 20, e.g., to rotate the latch 20 between the above-described first and second rotated positions. Advantageously, and as shown in, e.g., FIG. 2, only a topmost portion of the head 23 may protrude slightly from the first surface 11 of the spacer 10, thereby providing it with a very low profile.

Referring back to FIG. 1A, the head 23 of the latch 20 may include side surfaces around the sides of the head 23 and that are generally perpendicular to the surface of the head 23 that defines the tool-receiving opening 24. The side surfaces of the head 23 may include one or more planar surfaces 28 (as best shown in FIGS. 1A and 1B). In addition, the side surfaces of the head 23 may include at least one notch 25 defined therein. The side surfaces of the head 23 may include any number of notches 25, but in the embodiment shown in FIGS. 1A and 1B, define two notches 25 disposed on diametrically opposite sides of the head 23.

The implant 5 may also include a locking mechanism maintained within the spacer 10. In the embodiment shown, referring to FIG. 1A, the locking mechanism includes a pair of spring rods 30, although it is recognized that there may be provided, in other embodiments, one or more spring rods 30. In embodiments, the spring rods 30 may be formed from stainless steel or titanium. The spring rods 30 may reside within tubular cutouts or channels 18 that extend generally parallel to the axis Z and that are adjacent to and in communication with the latch housing 15. In addition, the spring rods 30 are movable within the spacer 10 such that, when the latch 20 is in the first above-described rotated position, the spring rods 30 engage the side surfaces, e.g., the plane surfaces 28, of the head 23 without entering the notches 25. In addition, the spring rods 30 may be further movable within the spacer 10 such that, when the latch 20 is in the second above-described rotated position, the spring rods 30 enter the notches 25 of the head 23 so as to prevent the latch 20 from further rotation, thereby increasing the locking force applied to the strap 50 within the spacer 20. The cutouts 18 define constricted ends 18*b* (best shown in FIGS. 5 and 6) into which one end of the spring rods 30 are inserted thereby constricting movement of this end of the spring rods 30. The cutouts 128 also define open ends 18*a* (best shown in FIG. 1A) on the opposite ends of the cutouts 18 (the end of the cutouts 18 that are positioned adjacent to the head 23 of the latch 20), which enable the spring rods 30 to flex freely into the latch housing 16 and into the notch 25 of the head 23.

As also shown in FIG. 1A, the latch 20 may also include a stud 26 located on its second end, e.g., an end of the latch that is opposite from the end having the head 23. The spacer 10 may also have a latch securing mechanism, such as a ferrule 40, that engages the stud 26 so as to prevent the latch 20 from exiting the latch housing 16. Additional details of such an arrangement are shown and described in connection with, e.g., FIGS. 3 and 4.

Referring to FIG. 1B, there are shown additional details of the flexible strap 50, in accordance with various embodiments. As set forth above, the spacer 20 may define at least one slot extending through the spacer 20 from the first side 10*a* to the second side 10*b*. In the embodiment shown in FIG. 1B, the spacer 10 defines a first slot 13, a second slot 14 and a third slot 19, each of the first, second and third slots 13, 14, 19 extending through the spacer 10 from the first side 10*a* to the second side 10*b* and each of the first, second and third slots 13, 14, 19 being configured to receive portions of the flexible strap 50 for engaging, e.g., wrapping around, the first and second adjacent interspinous processes. More specifically, FIG. 1B shows an embodiment in which the strap 50 has a folded end 54 that resides on the second side 10*b* of the spacer 10, the folded end 54 being larger than the openings of the second slot 14 so as to be prevented from being pulled through the second slot 14. The strap 50 then exits the second slot 14 on the first side 10*a* of the spacer 10 and eventually enters the third slot 19 on the first side 10*a* of the spacer 10. The portion of the strap 50 between the second slot 14 on the first side 10*a* of the spacer 10 and the third slot 19 on the first side 10*a* of the spacer 10 may form a first loop 51 of the strap 50 that is configured to loop around a first one, e.g., in the orientation shown, the upper one, of the adjacent interspinous processes.

Still referring to the embodiment of FIG. 1B, the strap 50 next exits the third slot 14 on the second side 10*b* of the spacer 10 and eventually enters the first slot 13 on the second side 10*b* of the spacer 10. The portion of the strap 50 between the third slot 19 on the second side 10*b* of the spacer 10 and the first slot 19 on the second side 10*b* of the spacer 10 may form a second loop 52 of the strap 50 that is configured to loop around a second one, e.g., in the orientation shown, the lower one, of the adjacent interspinous processes. Still further, the strap 50 may next exit the first slot 13 on the first side 10*a* of the spacer 10 so as to provide a free end 53 of the strap, ensuring that the strap 50 has enough length to accommodate patients of differing sizes.

Of course, it should be recognized that the strap 50 of the implant 5 may have other configurations. For example, the portion of the strap 50 that includes the free end 54 and that extends through the second slot 14 could, in other embodiments, be eliminated such as by eliminating the second slot 14 and instead attaching the strap 50 directly to the first side 10*a* of the spacer 10. Still further, in another embodiment, a configuration is envisioned having only a single loop of the strap and a single slot (thereby looping around only one, not both, of two adjacent interspinous processes). In this such embodiment, the second loop 52 of the strap 50 may be attached directly to the second side 10*b* of the spacer 10 at a location roughly where the strap 50 is shown in FIG. 1B as exiting the third slot 19, thereby enabling the third slot 19 to also be eliminated. In such an embodiment, the strap 50 would extend from a first connection point on the second side 10*b* of the spacer 10 through the first slot 13 so as to form the second loop 52 only, the second loop 52 looping around the lower (in the orientation shown in FIG. 1B) one of the two adjacent interspinous processes. Such a single loop-type embodiment could still provide some degree of vertebral stabilization to two adjacent interspinous processes, because the spacer would prevent the two adjacent interspinous processes from compressing relative to each other, while still allowing the two adjacent interspinous processes to expand relative to each other.

Figure 3:
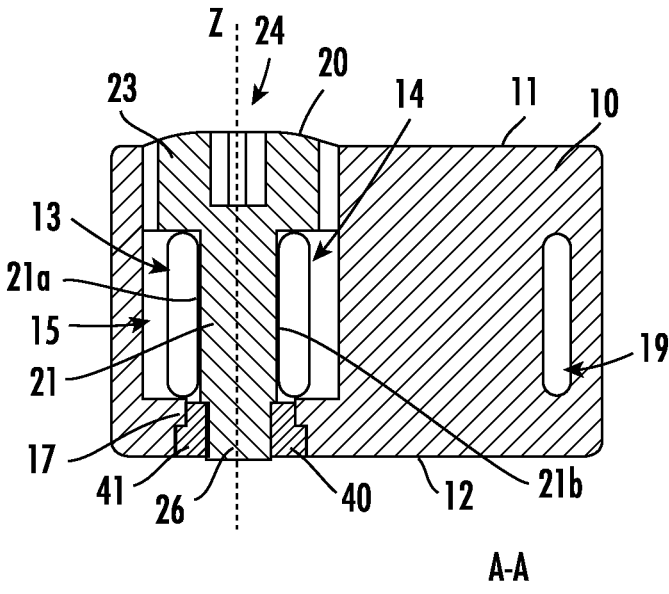
FIG. 3 shows a cross-sectional side view of the implant of FIG. 1A in an unlocked position.
Figure 4:
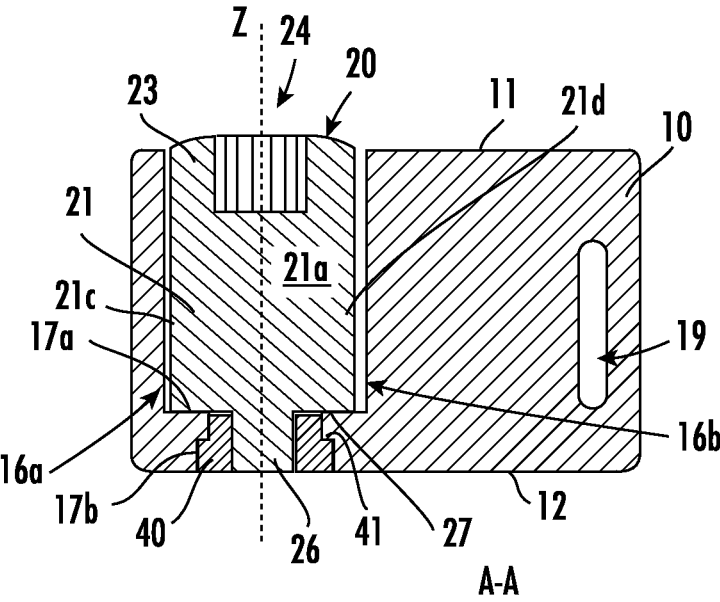
FIG. 4 shows a cross-sectional side view of the implant of FIG. 1A in a locked position.

As set forth above, FIG. 3 shows the implant 5 in cross-section along the plane A-A of FIG. 1B, with the latch 20 in the above-described first rotated position, e.g., a position in which the strap 50 (not shown in FIG. 3) is movable within the spacer 10. As shown in FIG. 3, in this above-described first rotated position, the latch 20 is oriented about the longitudinal axis Z such that the flat faces 21*c*, 21*d* are parallel with the first and second slots 13, 14, that pass through and intersect with the latch housing 15. In this embodiment, the width of the latch 20 between the flat faces 21*c*, 21*d* may be less than or equal to the distance between the first and second slots 13, 14, thereby enabling the strap to freely pass through the slots into the housing 15. A further view of these components in this above-described first rotated position is shown, e.g., in FIG. 5, which illustrates a cross-sectional view of the implant as taken along the plane B-B of FIG. 2.

Referring to FIG. 4, there is again shown the implant 5 in cross-section along the plane A-A of FIG. 1B, with the latch 20 in the above-described second, e.g., strap locked, rotated position of the latch 20. In this position, the latch 20 is oriented about the longitudinal axis Z such that flat faces 21*a*, 21*b* are now generally perpendicular to the first and second slots 13, 14, and with the curved faces 21*c*, 21*d* of the latch 20 directly facing the curved faces 16*a*, 16*b* of the latch housing 16. As set forth above, the distance between the curved faces 21*c*, 21*d* of the latch 20 and the curved faces 16*a*, 16*b* of the latch housing 16 is less than a thickness of the strap 50, such that the strap 50 is trapped between the curved faces 21*c*, 21*d* of the latch 20 and the curved faces 16*a*, 16*b* of the latch housing 16. In an embodiment, the distance between the curved faces 21*c*, 21*d* of the latch 20 and the curved faces 16*a*, 16*b* of the latch housing 16 may be 0.8 to 0.9 times the thickness of the strap 50. A further view of these components in this above-described second rotated position is shown, e.g., in FIG. 6 which also illustrates a cross-section of the implant in the plane B-B of FIG. 2.

Returning to FIGS. 3 and 4, the latch housing 16 of the spacer 10 has a bottom 17 defining a lower face 17*b*. A foot 27 of the latch 20 rests against the lower face 17*b* so as to prevent the latch from moving too far downwardly (in the view of FIGS. 3 and 4). In addition, the bottom 17 of the latch housing 16 defines a counterbore having a shoulder defining a lower face 17*b* against which rests a flange 41 of the ferrule 40 when the ferrule 40 is secured (e.g., by crimping, gluing, or other connection means) onto the stud 26 of the latch 20. Advantageously, and as shown, the ferrule 40 does not protrude beyond the second surface 12 of the spacer 20, so as to maintain a low profile. In this way, the ferrule 40 forms a means for retaining the latch 20 in the spacer 10, whereby the spacer 10 already fitted with its latch 20 may be implanted in a patient.

It is also noted that, while FIGS. 1A through 6 illustrate an embodiment in which the latch housing 16 has generally cylindrical bore configuration (with the latch 20 having a configuration that complements same), additional exemplary embodiments are also envisioned in which the latch housing 20 may have a generally conical configuration (e.g., with a cross-section reducing from the head 23 towards the foot 27 of the latch along the Z axis), while the latch 20 may have, e.g., second faces 21c, 21d that complement such generally conical profile.

Furthermore, while the illustrations show a single implant 5 in use with a pair of adjacent vertebrae 70a, 70b, it is understood that more than one implant 5 may be used at different levels of the spine to stabilize pairs of adjacent vertebrae. A system or kit comprising differently sized implants 5 may be provided so that different regions of the spine may be stabilized with the appropriately sized implant 5, for example.

There are no limitations in terms of the particular embodiments described in this application, which are intended as illustrations of various aspects only. Many modifications and variations can be made without departing from its spirit and scope, as will be apparent to those skilled in the art. Functionally equivalent methods and apparatuses, in addition to those enumerated herein, will be apparent to those skilled in the art from the foregoing descriptions. Such modifications and variations are intended to fall within the scope of the appended claims. Only the terms of the appended claims are intended to be limiting, along with the full scope of equivalents to which such claims are entitled. It is also to be understood that the terminology used herein, e.g., "and", "or", "including", "at least" as well as the use of plural or singular forms, etc., is for the purpose of describing examples of embodiments and is not intended to be limiting.

What is claimed is:

1. An intervertebral implant for stabilizing adjacent first and second interspinous processes, the implant comprising:
   a spacer having a first surface opposite a second surface, the spacer having a latch housing wall that extends from the first surface towards the second surface so as to define a latch housing within the spacer,
   the spacer having a first side opposite a second side, the first and second sides each configured to engage a respective one of the first and second adjacent interspinous processes,
   the spacer also defining first, second and third slots each extending through the spacer from the first side to the second side, each of the first, second and third slots configured to receive portions of a flexible strap for wrapping around the first and second adjacent interspinous processes; and
   a latch secured within the latch housing and configured to rotate about a latch axis between first and second rotated positions within the latch housing, the latch having first and second faces each positioned at different distances from the latch axis,
   wherein, when the latch is in the first rotated position, the first face of the latch faces the latch housing wall at a distance from the latch housing wall that is greater than the thickness of the flexible strap such that the strap is free to move between the first face of the latch and the latch housing wall, wherein, when the latch is in the second rotated position, the second face of the latch faces the latch housing wall at a distance from the latch housing wall that is less than the thickness of the flexible strap such that the strap is restricted from moving by and between the second face of the latch and the latch housing wall;
   wherein the latch includes a head surface having at least one notch defined therein; and
   a locking mechanism maintained within the spacer, the locking mechanism being movable within the spacer such that, when the latch is in the first rotated position the locking mechanism engages the head surface without entering the notch, and when the latch is in the second rotated position the locking mechanism enters the notch so as to prevent the latch from further rotation, wherein the locking mechanism is a spring rod fixed at one end within the spacer, the other end of the spring rod being movable into the notch.

2. The implant of claim 1, wherein the latch includes at a first end a head defining a tool-receiving opening, the tool-receiving opening configured to be engaged by a tool so as to rotate the latch between its first and second rotated positions.

3. The implant of claim 2, wherein the latch includes, at an end opposite from the head, a ferrule that maintains the latch within the latch housing.

4. The implant of claim 1, wherein the locking mechanism includes two spring rods disposed on opposite sides of the latch housing.

5. The implant of claim 4, wherein the latch head includes a plurality of notches defined around its circumference, such that the spring rods can move into any one of the plurality of notches so as to lock the latch relative to the latch housing in a plurality of different rotational positions.

6. The implant of claim 1, wherein the first face of the latch is flat.

7. The implant of claim 6, wherein the latch includes two flat first latch faces that are disposed on opposite sides of the latch relative to each other, the two flat latch faces being at a first latch face distance from each other.

8. The implant of claim 7, wherein:
   the first and second slots are spaced at a slot distance from each other,
   the first and second slots intersect with the latch housing, and
   the first latch face distance is less than or equal to the first slot distance, such that the flexible strap is free to move across both of the flat first latch surfaces.

9. The implant of claim 1, wherein the second face of the latch and the latch wall are both curved so as to be complementary relative to each other.

10. An intervertebral implant for stabilizing adjacent first and second interspinous processes, the implant comprising:
   a spacer having a first side opposite a second side, the first and second sides each configured to engage a respective one of the first and second adjacent interspinous processes,
   the spacer having first and second surfaces opposite to each other and perpendicular relative to the first and second sides, the spacer having a latch housing wall that extends from the first surface towards the second surface so as to define a latch housing within the spacer,
   the spacer defining at least one slot extending through the spacer from the first side to the second side, the at least one slot intersecting with the latch housing, the at least one slot configured to receive a portion of a flexible strap for wrapping around one or both of the first and second adjacent interspinous processes;

a latch positioned within the latch housing and configured to rotate about a latch axis between a first rotated position at which the strap is free to move between the first face of the latch and the latch housing wall, and a second rotated position at which the strap is restricted from moving between the second face of the latch and the latch housing wall;

a locking mechanism maintained within the spacer and configured to selectively engage the latch so as to prevent the latch from rotating within the latch housing when the latch is in the second rotated position;

wherein the latch has a head adjacent to the first surface of the spacer, the head defining a notch; and wherein the locking mechanism is a spring rod that is fixed at one end within the spacer, the other end of the spring rod being movable into the notch.

11. The implant of claim 10, wherein the spacer defines a channel in which the spring rod resides, and wherein, when the latch is rotated to a position at which the notch is aligned with the channel, at least a portion of the spring rod moves from the channel into the notch to prevent the latch from further rotating within the latch housing.

12. The implant of claim 11, wherein the locking mechanism includes two spring rods disposed on opposite sides of the latch housing.

13. The implant of claim 12, wherein the latch head includes a plurality of notches defined around its circumference, such that the spring rods can move into any one of the plurality of notches so as to lock the latch relative to the latch housing in a plurality of different rotational positions.

14. The implant of claim 10, wherein the latch has first and second faces each positioned at different distances from the latch axis, and wherein, when the latch is in the first rotated position, the strap is free to move between the first face of the latch and the latch housing wall because the first face of the latch faces the latch housing wall at a distance from the latch housing wall that is greater than the thickness of the flexible strap, and further wherein, when the latch is in the second rotated position, the strap is restricted from moving between the second face of the latch and the latch housing wall because the second face of the latch faces the latch housing wall at a distance from the latch housing wall that is less than the thickness of the flexible strap.

15. The implant of claim 14, wherein the first face of the latch is flat.

16. The implant of claim 14, wherein the second face of the latch and the latch wall are both curved.

17. The implant of claim 10, wherein the at least one slot comprises two slots, the flexible strap having a first portion extending through one slot and having a second portion extending through the other slot, and wherein both portions of the flexible strap that extend through the two slots are configured to be restricted from moving between second faces of the latch and the latch housing wall.

18. The implant of claim 17, wherein the spacer further defines a third slot, and a third portion of the flexible strap extends through the third slot, the flexible strap forming between the second and third slots a first loop around a first one of the adjacent interspinous processes, the flexible strap also forming between the third and first slots a second loop around a second one of the adjacent interspinous processes.

19. The implant of claim 10, wherein the latch includes a tool-receiving opening, the tool-receiving opening configured to be engaged by a tool so as to rotate the latch between its first and second rotated positions.

20. The implant of claim 10, wherein the latch includes, at an end opposite from the head, a ferrule that maintains the latch within the latch housing.

* * * * *